(12) United States Patent
Koninckx et al.

(10) Patent No.: US 8,911,358 B2
(45) Date of Patent: Dec. 16, 2014

(54) ENDOSCOPIC VISION SYSTEM

(75) Inventors: Philippe Koninckx, Bierbeek (BE); Thomas Koninckx, Blanden (BE); Luc Van Gool, Antwerp (BE)

(73) Assignee: Katholieke Universiteit Leuven, Leuven (BE)

( * ) Notice: Subject to any disclaimer, the term of this patent is extended or adjusted under 35 U.S.C. 154(b) by 873 days.

(21) Appl. No.: 12/373,036

(22) PCT Filed: Jul. 9, 2007

(86) PCT No.: PCT/BE2007/000079
§ 371 (c)(1),
(2), (4) Date: Jan. 8, 2009

(87) PCT Pub. No.: WO2008/006180
PCT Pub. Date: Jan. 17, 2008

(65) Prior Publication Data
US 2009/0259102 A1    Oct. 15, 2009

(30) Foreign Application Priority Data
Jul. 10, 2006    (GB) .................................. 0613576.8

(51) Int. Cl.
*A61B 1/00*    (2006.01)
*A61B 1/04*    (2006.01)

(52) U.S. Cl.
CPC .............. *A61B 1/042* (2013.01); *A61B 1/00193* (2013.01); *A61B 1/0005* (2013.01); *A61B 1/00181* (2013.01)
USPC ............ 600/113; 600/109; 600/102; 600/103

(58) Field of Classification Search
CPC .................. A61B 2019/507; A61B 2019/5289; A61B 2019/5291; A61B 2019/5293; A61B 2019/5295; A61B 2019/5297; A61B 19/5212; A61B 19/5244; A61B 19/56; A61B 1/00193; A61B 1/0005
USPC ............... 348/47, 48; 382/294; 600/103, 111, 600/117, 166
See application file for complete search history.

(56) References Cited

U.S. PATENT DOCUMENTS

| 4,697,577 | A |   | 10/1987 | Forkner |
| 5,305,121 | A | * | 4/1994  | Moll ................................ 348/45 |
| 5,313,306 | A |   | 5/1994  | Kuban et al. |
| 5,368,015 | A | * | 11/1994 | Wilk ............................. 600/104 |
| 5,524,180 | A |   | 6/1996  | Wang et al. |

(Continued)

FOREIGN PATENT DOCUMENTS

| WO | WO 2005/039391 A2 | 5/2005 |
| WO | WO 2005/084525 A1 | 7/2005 |

OTHER PUBLICATIONS

European Office Action for related EP 07784896.8, dated Jan. 22, 2014.

*Primary Examiner* — Anhtuan T Nguyen
*Assistant Examiner* — William Chou
(74) *Attorney, Agent, or Firm* — Bacon & Thomas, PLLC

(57) ABSTRACT

A multiple viewpoint endoscope system having a multiple viewpoint camera setup and/or an intelligent or cognitive image control system and display device particularly adapted for localizing internal structures within a cavity or an enclosing structure, such as an animal body, for instance the abdomen of an animal or human, or for localizing a real or synthetic image of such internal structures within an overview image or on an overview 3D model.

14 Claims, 8 Drawing Sheets

(56) References Cited

U.S. PATENT DOCUMENTS

| | | | |
|---|---|---|---|
| 5,653,677 A * | 8/1997 | Okada et al. | 600/112 |
| 5,682,199 A | 10/1997 | Lankford | |
| 5,749,362 A * | 5/1998 | Funda et al. | 600/407 |
| 5,764,809 A * | 6/1998 | Nomami et al. | 382/284 |
| 5,776,050 A | 7/1998 | Chen et al. | |
| 5,876,325 A | 3/1999 | Mizuno et al. | |
| 5,907,664 A | 5/1999 | Wang et al. | |
| 5,954,634 A | 9/1999 | Igarashi | |
| 6,066,090 A * | 5/2000 | Yoon | 600/113 |
| 6,097,423 A | 8/2000 | Mattsson-Boze et al. | |
| 6,371,909 B1 | 4/2002 | Hoeg et al. | |
| 6,428,470 B1 | 8/2002 | Thompson | |
| 6,494,826 B1 | 12/2002 | Chatenever et al. | |
| 6,503,195 B1 * | 1/2003 | Keller et al. | 600/160 |
| 6,591,130 B2 * | 7/2003 | Shahidi | 600/424 |
| 6,648,816 B2 * | 11/2003 | Irion et al. | 600/173 |
| 6,869,397 B2 * | 3/2005 | Black et al. | 600/168 |
| 7,494,338 B2 * | 2/2009 | Durbin et al. | 433/29 |
| 7,751,870 B2 * | 7/2010 | Whitman | 600/476 |
| 2002/0007110 A1 | 1/2002 | Irion | |
| 2002/0022767 A1 | 2/2002 | Dohi et al. | |
| 2002/0193687 A1 * | 12/2002 | Vining et al. | 600/425 |
| 2005/0165272 A1 * | 7/2005 | Okada et al. | 600/114 |
| 2005/0191046 A1 | 9/2005 | Dehmel et al. | |
| 2006/0293557 A1 * | 12/2006 | Chuanggui et al. | 600/101 |
| 2007/0021669 A1 * | 1/2007 | Miga et al. | 600/425 |
| 2007/0049795 A1 * | 3/2007 | Miyagi et al. | 600/109 |
| 2007/0149846 A1 * | 6/2007 | Chen et al. | 600/117 |
| 2007/0161854 A1 * | 7/2007 | Alamaro et al. | 600/109 |
| 2007/0161855 A1 * | 7/2007 | Mikkaichi et al. | 600/113 |
| 2007/0225553 A1 | 9/2007 | Shahidi | |
| 2008/0144773 A1 * | 6/2008 | Bar-Zohar et al. | 378/98.12 |

* cited by examiner a: patient
b: intra-abdominal cavity
c: trocar
d: insufflation
e: endoscope, camera, lighting Initialization multi-view setup

ENDOSCOPIC VISION SYSTEM

BACKGROUND OF THE INVENTION

A. Field of the Invention

The present invention relates to a novel endoscope or an optical large view endoscopic system with improved depth perception. In particular, a multiple viewpoint endoscope system comprising a multiple viewpoint camera setup and/or an intelligent or cognitive image control system and display device particularly adapted for localising internal structures within a cavity or an enclosing structure, such as an animal body, for instance the abdomen of an animal or human, or for localising a real or synthetic image of such internal structures within an overview image or on an overview 3D model.

B. Description of the Related Art

Endoscopy refers to techniques used to inspect or to look into internal cavities or hollow structures. Endoscopy is used today for medical applications and for industrial applications such as for instance in the visual inspection of aircraft, diesel and automotive engines by so called borescopes (boroscopes). In the medical field endoscopes are used for life saving inspections and interventions such as endoscopic surgery on organs in a patient's body cavity. Borescopes allow preventive maintenance or inspection work where the area to be inspected is inaccessible by other means. They can for instance be used for preventive maintenance and inspection tasks on targets within an enclosed structure such as aircraft engines and others which require particular attention because of safety requirements. In the remainder of this text only the medical field will be used to illustrate the new apparatus. Its applicability, however, extends without limitations to the industrial working domain.

Medical endoscopic surgery, also called minimal access surgery has become widely used over the last decade because of clear-cut advantages such as a decreased postoperative morbidity, less pain and a shorter hospitalisation. Endoscopic surgery, however, is technically more demanding than 'classical open surgery' for several reasons such as smaller instruments, and the limitation of the smaller entry ports. The learning curve of endoscopic surgery is much longer than expected a decade ago.

A crucial problem remains the monocular vision with limited depth perception, together with a small field of view also referred to as 'tunnel vision'. Normally surgeons work with a camera acquiring video data through the endoscope, and perform surgery on a video display. This causes most depth of vision cues to be lost. The small field of view leads to difficulties of orientation and surgical mistakes. Experimentally, we were able to demonstrate in a rabbit nephrectomy model that the duration of surgery, bleeding and accidents increase when the fields of view becomes smaller. This increase in duration of surgery and in accidents as a consequence of the small field of view decreases with the experience of the surgeon, suggesting that with experience and training the human brain is capable of reconstructing to a certain extent a broader field of view from the video data given. Unexperienced surgeons perceive this problem much more since they are not able to mentally reconstruct such an overview of the working field. Another limitation of the small field of view is the difficulty to position instruments into the field of view: surgery is performed with the lens at a short distance of the target tissue, eg 2 to 3 cm in order to obtain a sharp enlarged image. To position an instrument "blindly" in this field of view requires a lot of experience and training. The alternative is to zoom out to visualize the instrument and then to zoom in again maintaining the instrument in the field of view. It is obvious, that this requires time, slowing down the surgery. During emergency cases eg an important bleeding, this becomes crucial: the artery should be clamped within seconds with the camera at short distance for visualization. If this fails, the operating field is flooded with blood, making things more difficult. This is the main reason why in gynaecologic surgery, for hysterectomies the conversion rates (ie to change from laparoscopy to laparotomy) range from 0 to 30% according to the experience of the surgeon.

Implementations of non-monocular vision through an endoscope are in general embodied as a stereo setup. Two nearby optical pathways provide a baseline and therefore show two different real, but nearby viewpoints. If presented respectively to the left and right eye, this leads to depth perception for a human observer. However, this approach has several drawbacks, like ego the need for an endoscope with a larger cross section or with smaller optical pathways. Moreover, stereoscopic visualization has no transparent implementation yet and requires eg shutter glasses, auto-stereoscopic displays or head mounted displays. Today these approaches to 3D visualization have failed to become widely accepted in endoscopic surgery because too cumbersome and too expensive without real demonstrable benefits.

The limitation of a restricted view has been addressed historically by building wide angle lenses. These have the drawback, however, that a close up view can only be obtained with the lens at a short distance from the tissue, thus making the working distance, i.e. the distance between lens and tissue limited. Another approach is by using with the endoscopes a varifocal camera unit or by using lenses with different focal lengths. This provides a surgeon with an optical zoom, and allows to restrict or enlarge the working field. However, zooming and refocusing is not straightforward per-operatively and is no real option to get a quick overview of the scene. Indeed if one hand holds a camera with a lens, a second hand is needed to adjust the angle of view; this second hand thus is no longer available for surgery. A zoomed out camera view—even if used with larger monitors—is not practical to work with.

The problem thus narrows down to the dilemma, that we need a high resolution essential to work. This requires either a wide angle at short distance or a narrow view at larger distance. The former solution limits the working space, the latter solution makes an overview picture practically impossible. Today lenses and camera units with a variable field of view exist but are not really used for practical reasons.

More recently so called 'capsule endoscopy' has been introduced. This technique normally refers to the concept of 'a camera in a pill'. The device is swallowed and travels independently the internal digestive system. During this passage video data (and eventually supplementary data) are being collected and either stored in local memory or send to a receiver using a wireless link. One of the promoter applications of this technique is the inspection of the small intestine eg to check whether anemia could be caused by intestinal bleeding.

PROBLEM SUMMARY

Despite the advanced stage of current systems for video endoscopy there is a need in the art for videoendoscopes or videoborescopes that ascertain ease and safety of critical operations by providing an accurate depth perception and ease of positioning the instruments in the field of view. Moreover the working field is limited and there is no means to visualize instruments outside this field of view and still keep a high resolution image of the local working field. No method or apparatus currently can generate either an overview image of the endoscopic working volume, or multiple different viewpoints of the endoscopic working volume. Neither are there existing systems for endoscopic 3D acquisition, which can generate quantitative SD measurements, and this through an unmodified mono focal endoscope, even in case of a deformable environment. The difference with stereo endoscopy or stereoscopic endoscopy and visualisation will be explained later in this text and mainly relate to the relative distance between the different lenses and the size of the object. In endoscopic stereo systems the lenses are near to each other when compared to the relative size of the objects, in the system of present invention this is no longer the case. In a stereo endoscope the two centers of the lenses are typically some 10 mm apart, whereas now we can separate the lenses up to 50 mm or more. Moreover the distance between the lenses is not fixed at construction time, as is the case in a stereoendoscope but can be fixed at deployment time, or even can be changed during operation. This is by no means possible in case of a stereo system. Also the system is by no means limited to the use of two lenses or cameras only, as is the case in a stereo endoscope, but can use multiple different cameras at the same time.

Present invention provides solutions to the aforementioned problems by combining a high resolution video stream of the local working field (local zoom in) together with a general overview of the overall scene (zoom out) and this without the need for additional incisions and the possibility to shift the region of interest without physically moving the optics. Moreover it can generate 3D information of a moving and deformable endoscopic scene with an unmodified mono focal endoscope and the multi view camera setup.

SUMMARY OF THE INVENTION

The present invention relates to the process or a system for image formation in endoscopy and more specifically a process or system which allows to synthesise (extreme) wide angle mosaic images (also referred to as panoramas or synthetic overview images) of internal structures in a body, for instance the internal organs in the body of an animal or human subject.

The system comprises a multiple viewpoint camera setup and an intelligent or cognitive image control system integrated into an endoscope—a device for endoscopic surgery—, to generate synthetic viewpoints or overview images. The system of present invention provides a solution to localise the current real or synthetic image of such internal structures with respect to these overview images.

Moreover the system can generate endoscopic 3D measurements and visualisations, through an unmodified mono focal endoscope and the multiple viewpoint camera setup, or by means of mono focal endoscopic pattern projection and the multiple viewpoint camera setup. This is again different from any prior endoscopic pattern projection systems, where the baselines (camera—projector lens distance) is typically in order of 10 mm whereas now we can increase it up to 50 mm or more.

The system of present invention can be integrated in existing (video)endoscopic systems. A video endoscopic system that is particularly suitable to be adapted for the present invention is a video endoscopic system comprising an endoscopic optical system and a camera. In such a system the endoscopic optical system having an elongated shaft through which an optical image guide and a fiber light guide extend, and an end housing, which is proximally connected to the shaft and has an image exit window and a light entry window, the camera portion including a camera housing, extending from which are an image signal cable and a light guide cable, and an image entry window and a light exit window. The end housing and the camera housing carrying co-operating rotationally lockable coupling means, arranged to couple the housings together and to lock the housing in a relative rotational position in which the image entry and exit windows are in alignment and the light entry and exit windows are in alignment. The coupling means including a cylinder with an end wall on one of the housings and a complementary bore with a base wall in the other housing, the windows being arranged in the end wall of the cylinder and the base wall of the bore. Such has been described in US20050191046.

The imaging system of present for receiving selected images of said selected portion of a field of view of a internal structure of an enclosing body and for producing output signals corresponding to said selected images to the image capture circuitry of present invention for receiving and providing digitized signals from said output signals from said imaging system and the image transform circuitry of present invention for processing said digitized signals from said image capture circuitry can be integrated in or connected to a (microtelescopic) laparoscope, endoscope or borescope. Such a laparoscope, endoscope or borescope can be for instance of the type that comprise a) an elongated tube with an observation head in which the image capture circuitry can be integrated; b) elongated optical conduit means connecting said head and image capture circuitry to said image capture circuitry. The elongated insertion tube can contain optical means for conducting an optical image of the target on an enclosed structure (eg internal structure in a patient's body) from an imaging system at a proximal end (from the target) of the insertion tube to an image acquiring circuitry at a distal end thereof and it may also comprise a light conduit means therein for conducting illumination for a distal light tube fitting to said proximal end (proximal to the target) of the insertion tube to illuminate said target.

Other systems of videoendoscopy which can be adapted by the system of present invention are disclosed in U.S. Pat. No. 5,682,199 and U.S. Pat. No. 6,494,826 B1. These prior systems both consist of an endoscope optical system and a camera housing which may be connected by means of a coupling, whereby both the image is coupled in one direction and the light is coupled in the other direction through the coupling point with appropriate windows. Separate elements suitable for the videoendoscopic system of present invention have been described in U.S. Pat. No. 4,697,577, U.S. Pat. No. 5,313,306, U.S. Pat. No. 5,524,180, U.S. Pat. No. 5,776,050, U.S. Pat. No. 5,876,325, U.S. Pat. No. 5,907,664, U.S. Pat. No. 5,954,634, U.S. Pat. No. 6,097,423, U.S. Pat. No. 6,371,909, U.S. Pat. No. 6,428,470 and US20020022767.

An apparently related system with respect to the endoscopic 3D depth extraction has been described in U.S. Pat. No. 6,503,195. The major differences with respect to the 3D computation relates to the baseline(s) (cfr inf) being used (the multiple view endoscopic setup is a so-called 'wide baseline' setup) and therefore the different system for 3D computation and the number of viewpoints (the multiple view endoscopic setup is by no means restricted to a single camera, or to a single camera and projection device). Moreover, the system referenced above uses an adapted endoscope whereas the present invention can work with an unmodified mono focal endoscope. In other words there is no need for a stereo camera or stereo acquisition device for the multi-view setup to work, and generate 3D information. This said the system still can work with images coming from a stereo camera.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

Present invention comprises an endoscopic method that instructs one or more persons carrying out surgery respectively on the primary camera providing a picture of an internal part of the body, on the secondary camera(s) providing a picture of another internal part of the body to another display means, both pictures being integrated in an overview picture or model, shown on the displays of the internal body or being shown independently. In a particular embodiment a control system transforms the multiple video streams of the cameras into a synthetic wide angle overview image. In yet another embodiment the method extracts 3D information from multiple images, not all coming from a camera mounted to the endoscope. In the remainder of the text the camera mounted to the endoscope will be mostly referred to as the principal or primary camera, whereas the other are referred to as secondary or multi-view cameras. The latter can be inserted into a cavity through the entry port of the primary camera, without the need for additional entry ports. Insertion can also be done comparable to the primary camera using secondary entry ports and cameras outside the cavity, with a lens protruding the cavity wall. Alternatively the method generates 3D information based on the projection of structured light through a regular unmodified mono focal endoscope, while imaging the scene through a multi-view endoscopic camera network or the method generates 3D information based on the projection of structured light through a stereo endoscope, while imaging the scene through one optical channel of the endoscope, and projection though the other optical channel. In yet another embodiment the method extracts 3D information without active illumination, and only uses the different camera images therefore. In the latter embodiment one of the cameras can also be moving with respect to the set of other cameras, which comprises at least two non moving cameras.

The endoscopic method of present invention can also be used to localize a moving endoscope w.r.t. a real or synthetic wide angle camera image. Furthermore it can determine the constellation of an N-camera multi-view setup, and to derive automatically a camera calibration for this setup By the invention of present method it also is possible to generate one or more virtual, possibly moving, camera images, without the need for motion of any optical components in an endoscopic working domain.

The method of present invention is particularly suitable to implement a safety procedure to warn a user when a real or imaginary boundary is crossed. This is done using the above technique for localisation of the moving endoscope wrt the overview image.

The present invention can be an endoscopic or borescopic vision system for inspecting the inside of a cavity or guiding operation on enclosed structures in said cavity, comprising an imaging system for receiving selected images of a target object and to create said output signals of the object image which is characterised in that the imaging system comprises a camera system designed to create said output signals of different object images of portions of the target structure or the direct environment thereof, whereby the camera system comprises a first ocular system (lens or camera) and at least a second ocular system (lens or camera) of which the distances between the both ocular systems are not fixed but whereby at deployment or in operational working state the optical distance is above 10 mm, preferably above 20 mm, more preferably between 20 and 200 mm, yet more preferably above 40 mm, for instance between 40 and 200 mm and most preferably above 50 mm for instance 50 and 100 mm.

Yet another embodiment of present invention is an endoscopic or borescopic vision system for inspecting the inside of a cavity or guiding operation on enclosed structures in said cavity, comprising an imaging system for receiving selected images of a target object and to create said output signals of the object image which is characterised in that the imaging system comprises a camera system designed to create said output signals of different object images of portions of the target structure or the direct environment thereof whereby the camera system comprises a first ocular system (lens or camera) and at least a second ocular system (lens or camera) whereby at deployment or in operational working the relative viewpoints of said ocular systems can be modified to generate views which do not share any common structures in the scene. In a preferred embodiment this is achieved by changing the ocular distances between the ocular systems or the orientation of one or more ocular systems. This is under normal working situations not possible with for instance a stereo system.

BRIEF DESCRIPTION OF THE DRAWINGS

The present invention will become more fully understood from the detailed description given herein below and the accompanying drawings which are given by way of illustration only, and thus are not limitative of the present invention, and wherein.

Figure 1:
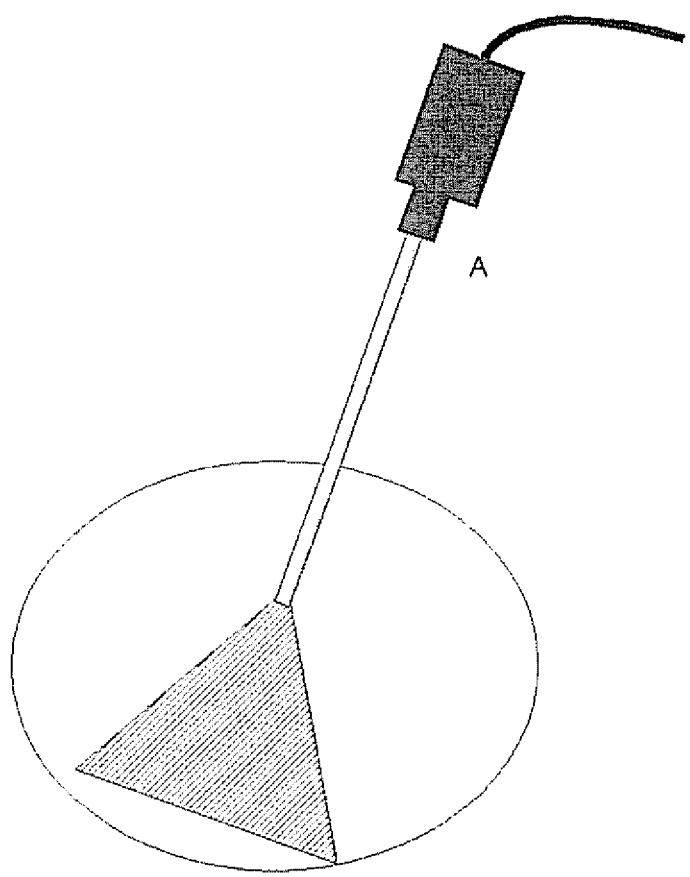
FIG. 1 is a schematic view showing a normal endoscopic working volume, using an external camera (A) and an endoscopic telescope to provide an image of the internal cavity. The hatched region is a representation of the camera frustum, indicating the part of the working volume visible in the camera images without moving the optics.

The drawing represents a perforated base plate with centrally the secondary multi-view camera. This is a more convenient means of fixating this secondary camera, than a regular capsule device. However, this is by no means the only way of providing such fixation.

Figure 6:
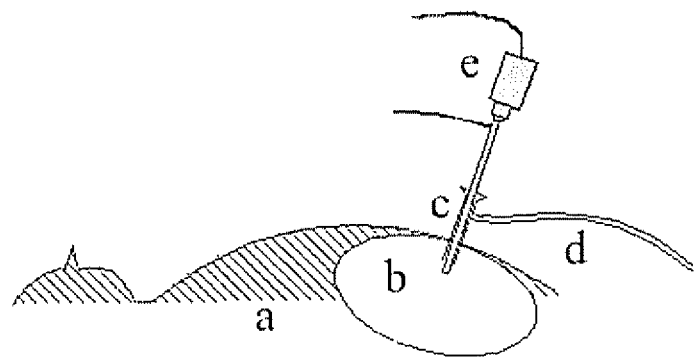

FIG. 6 is a schematic view showing the endoscopic working setup in laparoscopy, indicating the major units related to the field of this invention and its embodiment in laparoscopy, and their relationship to the patient. It is intended to provide a better understanding of the overall endoscopic working circumstances.

Figure 7:
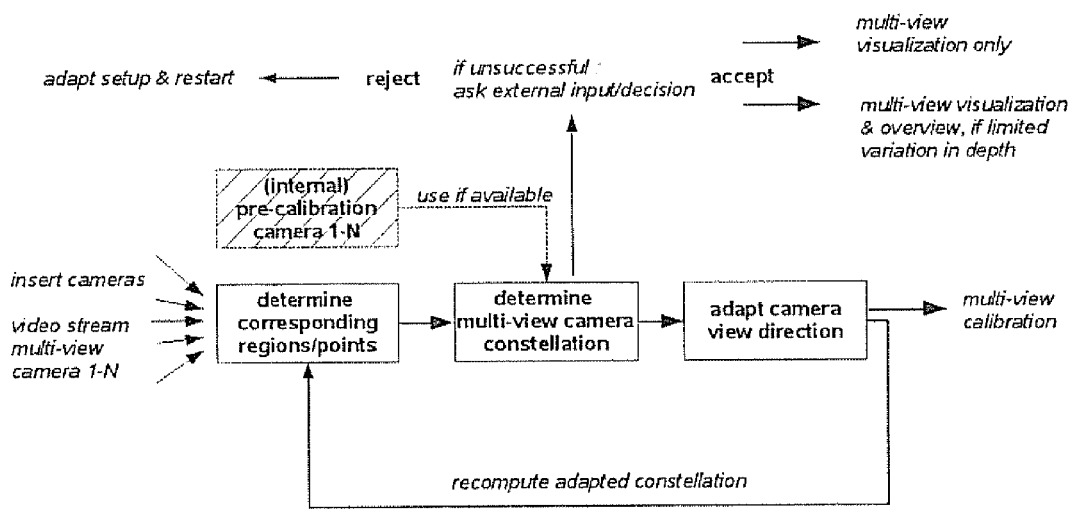

FIG. 7 is a flowchart explaining the initial setup, calibration and verification of the N-view constellation. Its implementation will be explained in more detail in the remainder of this text.

Figure 8:
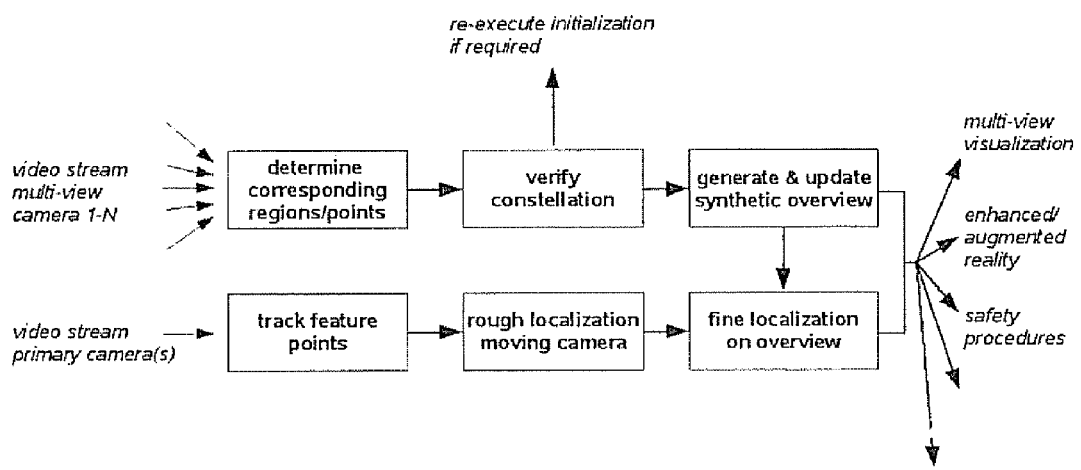

FIG. 8 is a schematic view showing the main functional steps required by the 'Cognitive Control Unit' in order to generate the synthetic overview image, the 3D information derived from the endoscopic scene or the localisation of the moving primary camera wrt the overview image or 3D model.

DETAILED DESCRIPTION OF EMBODIMENTS OF THE INVENTION

It will be apparent to those skilled in the art that various modifications and variations can be made in process and methods of the present invention of a multiple viewpoint endoscopic camera system, or simply multi view endoscope and its use for generating of synthetic overview images or for generating endoscopic 3D information, and in construction of the system and method without departing from the scope or spirit of the invention. Examples of such modifications have been previously provided.

Other embodiments of the invention will be apparent to those skilled in the art from consideration of the specification and practice of the invention disclosed herein. It is intended that the specification and examples be considered as exemplary only.

Image (based) correspondences for the meaning of present invention are points in two or more different views which correspond to the projection of the same physical world point into these views. Their representation is a vector of M position coordinates in the different images, with M the number of images between which the 'correspondence' for this point could be established. The process of establishing correspondences is also referred to as 'matching'. In case a corresponding point for every image pixel is searched, the latter is referred to as 'dense matching'. The image data can originate from still pictures or from video. The same definition is used if one or more cameras are replaced by projection devices. In this case the correspondences refer to points in two or more views or projection patterns, which project upon or are the projection of the same physical world point.

Interocular distance for the meaning of present invention is the distance between the oculars of optical instruments or the distance between the lens or camera centers.

Camera calibration for the meaning of present invention is the process of deriving the set of parameters which describes the image formation process of an imaging device (a camera, a video camera, an endoscopic imaging unit, . . . ). The complete set of techniques presented here for extended image based scene interpretation only become feasible after a successful camera calibration.

A 3D model for the meaning of present invention is a geometric description of a scene which provides a three-dimensional location of a discrete set of points with respect to a reference point (reference of the coordinate system). Depending on the application the colour data is considered part of or supplementary data wrt the 3D model. In the latter case the resolution of both can be different. When compared to an image (which only stores colour information), this is a richer representation of the scene. An integrated 3D model can combine more data than what can be represented in a single camera view (eg the back and frontal side of an object). Although a 3D model can be used to generate a stereo visualisation, it is fundamentally different from mere stereo acquisition. The former refers to a AD scene analysis (a measurement), the latter is only a recording from two slightly different viewpoints and provides no scene interpretation or analysis (stereo). Terminology however can be misleading, as a stereo acquisition when presented to a human observer offers depth perception. Therefore a stereo endoscope together with a stereoscopic visualisation unit, is often referred to as a '3D endoscopic system', although it does not provide any 3D measurement or analysis of the endoscopic scene other than by the human brain. Within this text we refer to quantitative measurements.

Frame rate, or frame frequency, for the meaning of present invention is the measurement of how quickly an imaging device, such as computer graphics, video cameras, film cameras, and motion capture systems, produces unique consecutive images called flames. The term applies equally well to an endoscopic imaging device. Frame rate is most often expressed in frames per second or simply, hertz (Hz).

A Cognitive Control Unit for the meaning of the present invention is a unit which transforms taw image data coming from one or multiple cameras into a single enhanced representation. Instead of presenting the user with more information, it combines and offers enriched information. The latter avoids flooding the human observer with too many individual streams of information such that interpretation becomes infeasible. An illustration where the latter typically can happen is a control wall for video surveillance. Presenting the different raw video streams of the multi-view camera network could lead to a similar situation. A key element which distinguishes this unit from alternative implementations is that it uses (local or distributed) intelligence to do this merging of video data based on scene interpretation. Therefore it is referred to as a cognitive unit. It is a control unit, as it introduces feedback based on its computed output to adapt or control the camera system. The level of image based interpretation needed to do so is comparable to what a human observer mentally does, and surpasses any straightforward regulatory action like eg intensity control and similar actions found in nowadays so called 'endoscopic video processors'. Illustrative examples are the construction of an integrated overview image or mosaic (sometimes also referred to as a 'panorama') of the scene, measuring a 3 D model of the scene, etc Mono focal refers to an optical system with a single optical pathway, whereas in stereo two optical pathways are used.

The baseline for the meaning of the present invention is the translation vector, (or its magnitude, depending on the context) relating the individual effective optical camera centers as obtained by the camera calibration of the different devices in a system comprising multiple cameras, or multiple cameras and a projector or multiple cameras and projectors. Effective optical camera center hereby refers to the location of the lens center as computed during the camera calibration using eg a calibration technique as described in "An Efficient and Accurate Camera Calibration Technique for 3D Machine Vision, Roger Y. Tsai, Proceedings of IEEE Conference on Computer Vision and Pattern Recognition, Miami Beach, Fla., 1986, pages 364-374". Such a system is referred to as a wide baseline system if the baseline or baselines is/are of comparable size when compared to the structures in the scenes being imaged or projected on. Such condition may also imply a large rotation angle between the optical axes of the different cameras, in order to have the same scene in the field of view.

Mono focal refers to an optical system with a single optical pathway, whereas in stereo two optical pathways are used.

The baseline for the meaning of the present invention is the translation vector, (or its magnitude, depending on the context) relating the individual camera centers of the different devices in a system comprising multiple cameras, or multiple cameras and a projector or multiple cameras and projectors. Such a system is referred to as a wide baseline system if the baseline or baselines is/ale of comparable size when compared to the structures in the scenes being imaged or projected on. Such condition may also imply a large rotation angle between the optical axes of the different cameras, in order to have the same scene in the field of view.

A system has been developed to generate multiple (minimal two) internal views, with a difference in viewpoint which is much larger than available in stereo endoscopy. More specifically a regular stereo endoscope will have a baseline which is an order of magnitude (scale factor ×10) smaller than the internal structures imaged. The current invention envisions baselines which can be of similar sizes compared to the structures being imaged and which moreover is adaptable. For medical applications this boils down to be an increase in baseline from the range of 5 to 20 mm to an extended range of 5 to 250 mm. This allows the system to generate much more fundamentally different viewpoints. The latter means that the images generated are not just similar with only a slight deformation with respect to each other; but really visualise a different part of the scene. Whereas in case of stereo imaging, typically about 75% or more of all image pixels can be related to a pixel of the secondary image by computing the corresponding local image deformation, this will no longer be the case. Hence we refer to 'fundamentally different viewpoints', originating from the relative so called 'wide baseline' setup. This said, as the baseline is adaptable and the relative orientation of the different cameras can be changed, the multi-view system can, but is not enforced to be used as a wide-baseline setup. In combination with the aforementioned cognitive image control system, this leads to a completely new endoscopic visualization.

Figure 2:
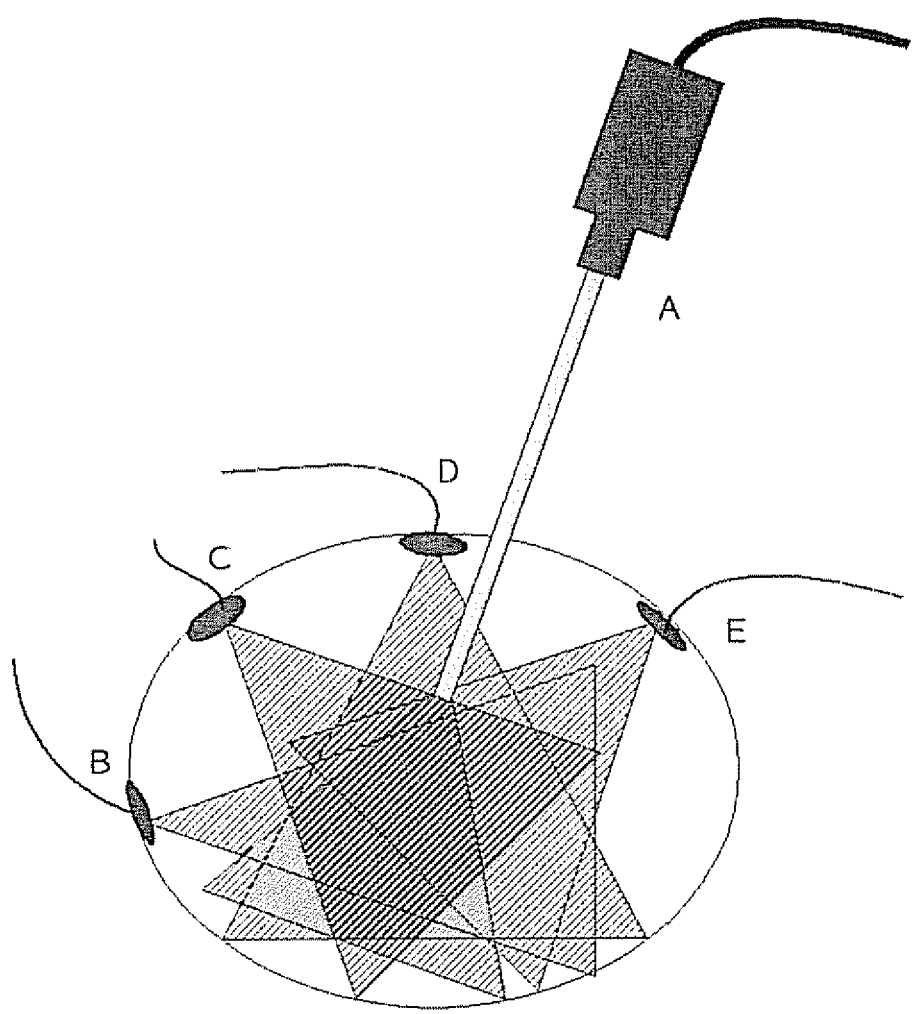
FIG. 2 is a schematic view showing the same endoscopic working volume of FIG. 1 but with a N-view endoscopic multi-view setup, with N=5. The regular endoscopic camera (A) is referred to as the primary camera, whereas cameras (B-E) are secondary multi-view cameras. The working volume visible in a camera feed now is the envelope of all camera frusta, and spans a much larger visible area. Signal and power wiring is transferred through the cavity wall, and can be used as a means to provide fixation.

This endoscopic system works with minimally two different cameras. The system can function with multiple cameras. For instance, it can use an extended camera array if the working field allows for their insertion. The use of up to six cameras seems to provide a reasonable trade-off between quality and system complexity. However, there is no theoretical upper bound of the maximum numbers of cameras that can be used. The latter rather is restricted by practical issues like e.g. the amount of computing power available. This said neither the implementation nor the application of present invention targets the implementation or application of image processing to achieve only stereo acquisition or visualization. But the system of present invention has as a particular advantage that availability of multiple different video sources makes it possible to carry out an operation based on a principal or primary camera image, while the secondary cameras provide a different image of another part of the targeted internal structures. The system of present invention does not have to be limited to two viewpoints only, but it extends to N viewpoints. Moreover, the secondary camera or cameras can have a different zoom and orientation and such can provide an overview image. For the secondary cameras either capsule based devices are used or (regular) endoscopic lenses and cameras, inserted through secondary entry ports. In the latter case the secondary endoscopes will preferably have a smaller section (eg 2 mm) than the primary endoscope (eg 10 mm). The original images can be presented to the surgeon and her/his staff as independent video streams, or are fed into the control unit which combines the different streams into a single new composite overview video image. This provides an enhanced visualization in which both a high resolution video of the working field is combined with a larger overview image (see FIG. 2). This enhanced view is equipped with a steerable region of interest, which makes the working field selectable without moving optical components. This functionality is provided through the cognitive control unit, and is only feasible using the multi-view camera setup. This cognitive aspect of the overall endoscopic system and the implementation by which it can be achieved is the core of the invention embodied within this apparatus. It comprises the interpretation of the scene necessary to generate the overview image. Moreover it can additionally provide an approximate or accurate dense 3D scene analysis. The cognitive control unit is a device implementing distributed or local intelligence, and such provides a means for image analysis. The most straightforward implementation comprises a software implementation and a processor for its execution, given the real-time constraint introduced by the processing of streaming video is respected. The latter is dependent on the number of parallel camera feeds to be processed. To this end a software implementation of the logic and intelligence in combination with dedicated, or configurable signal processors is advisory. Optimally the control unit can even be completely hard coded in a dedicated signal processor, requiring limited or no software configuration. Essential for the implementation, however, is the streaming processing which requires real-time performance, without introducing noticeable input-output delay. A guideline for the former is a minimal framerate of 15 hz, whereas the delay should be reduced to be smaller than approx 30 msec. Otherwise we found out during experiments that the videostream is not perceived as being fluent enough by medical users. Moreover tests demonstrated that in case of larger delays, a human observer notices the de-synchronisation between hand movements and visual appearance while performing surgery. This said, whatever the concrete implementation of the control unit is—software & processor, software processor and signal processor, hard coded implementation, or a combination—can be selected on the basis of other considerations, as long as the real-time constraints are respected, and the image based logic is correctly executed An embodiment of present invention is thus an endoscopic or borescopic vision system for inspecting the inside of a cavity or guiding operation on enclosed structures in said cavity, comprising an imaging system for receiving selected images of a target object and to create said output signals of the object image that is characterised in that the imaging system comprises a camera system designed to create said output signals of different object images of portions of the target structure or the direct environment thereof, whereby the camera system comprises a first ocular system (lens or camera) and at least a second ocular system (lens or camera) whereby at deployment or in operational working the ocular distances between the ocular systems are controllable to change the different viewpoints relatively to each other. This ocular systems may controllable to change the different viewpoints relatively to each in such to generate views which do not have image correspondences or which do not share any common structures or which do not share in the scene.

A particularly suitable endoscopic or borescopic vision system is such as above but whereby the distances between the both ocular systems can change but whereby at deployment or in operational working state the optical distance is above 20 mm. In a preferred embodiment such endoscopic or borescopic vision system is characterised in that the distances between the both ocular, systems can change but whereby at deployment or in operational working state the optical distance is above 50 mm.

EXAMPLES OF SELECTED ILLUSTRATIVE EMBODIMENTS OF A MULTI VIEW ENDOSCOPIC SETUP AND THE OPERATION OF THE COGNITIVE CONTROL UNIT

Example 1

Multiview Endoscopic Visualisation with Fine Tuning of the Multi View Camera Network Embodiment of the Invention in Laparoscopy In laparoscopy, being endoscopy in the abdominal cavity, endoscopes are normally rigid with a camera outside the body. The endoscope is inserted through a single small incision. Additional incisions allow to insert specific endoscopic (surgical) instruments. The working field contains considerably large variations in depth, relatively to the standoff (distance between tissue and lens) of the endoscopic telescopic lens. The telescope is used to visualize a particular region of interest within the abdominal cavity. This means that secondary regions are not visible to the surgeon or her/his staff. Nevertheless it often occurs that one or more assistants are keeping structures away outside the field of view. In such case this is done without any vision based feedback for neither the surgeon nor her/his assistants. The same reasoning applies when surgery is performed very close to vital or fragile organs and structure (eg the ureters, veins, nerves, etc. . . . )

Figure 3:
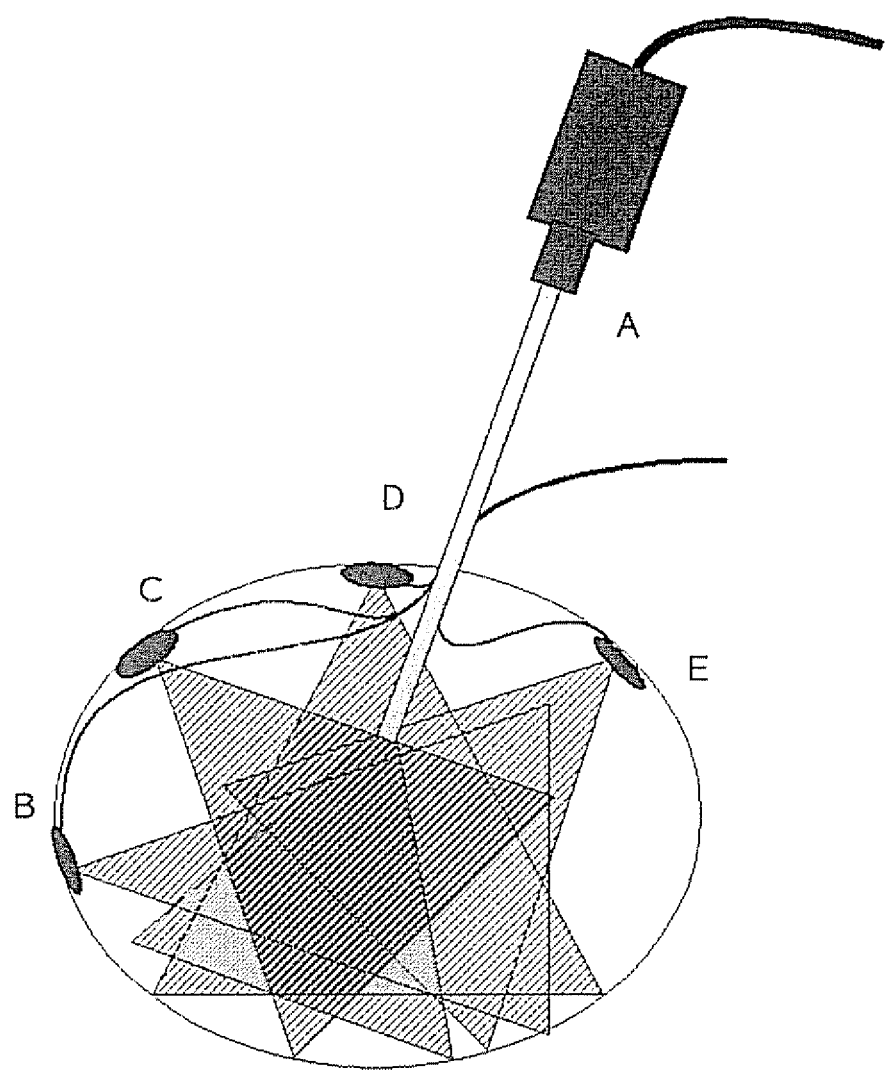
FIG. 3 is a schematic view showing the same endoscopic working volume of FIG. 1 and FIG. 2 but with the wiring guided as a single string through the trocar.

The apparatus of present invention implements a way to avoid this partially blind operation. To this end one or more secondary cameras are inserted into the body though the same incision as used to insert the regular endoscope (see FIG. 3). Devices derived from endoscopic capsule cameras with a 40 degree re-orientable head are suitable as secondary cameras. Alternatively secondary entry ports to the body can be used, with regular—possibly thin cross section—endoscopes.

Figure 5:
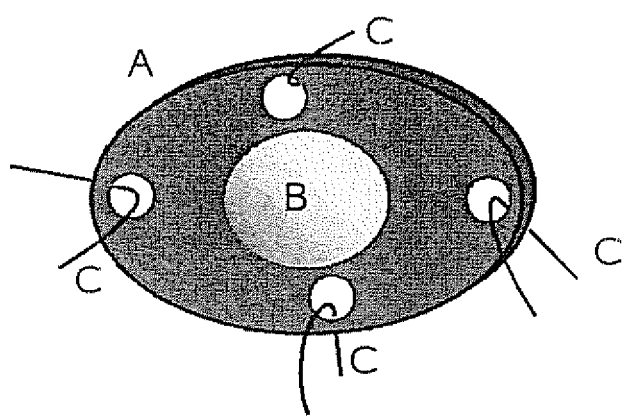
FIG. 5 shows a possible configuration which allows fixating the secondary multi-view cameras referenced in FIG. 3.

For low frame rates or frame frequencies wireless transmission is used in case of capsule devices, whereas for fluent video rates the same devices in a wired configuration are used. In laparoscopy or borescopy the wiring is guided as a joined string through the trocar or entry shaft to the cavity (see FIG. 3), or as per camera signal wire (see FIG. 2) directly through the abdominal wall or cavity wall. In the latter case the signal and power wiring provides also fixation. In the wireless case this fixation is done using one or more stitches. To this end the camera housing provides a ways to fixate them, and the shape is adapted for adhesion to the abdominal wall (see FIG. 5 for an illustration). The internal configuration of the secondary cameras loosely defines the new overall integrated working field that will become available. The re-orientable camera heads allow the system to automatically fine-tune its configuration (e.g. its field of view). The fine tuning is steered by a new algorithm minimising the distance between the intersection points of the different optical axes (center lines) of the lenses in the multi view camera system (cfr. inf.). It is executed by the cognitive control unit. Internally the cognitive control unit will extend the outcome of, and work further on, algorithms known within the community of computer vision, and which are commonly referred to as 'wide base line matching', 'dense matching', 'affine invariance', 'camera auto calibration', 'camera auto calibration with internal pre calibration' and 'shape from video'.

In case the implementation uses the same devices with fixed camera heads, or in case of use of regular endoscopes through secondary entry ports, the additional fine timing is not longer possible but the overall functionality would be still available, albeit in a restricted form. After insertion the apparatus first runs a self configuration, during which an image based mutual localisation of the N cameras is performed followed by the fine tuning of the configuration.

Therefore the optical endoscopic or borescopic system of present invention comprises a turnkey technique to find corresponding regions, eventually refined to corresponding points between the different cameras. To this end the control unit performs a so called wide baseline matching using 'invariant regions'. By a combination of multiple different techniques (SIFT/SURF/affine invariance) better performance and robustness is obtained, due to self checking and voting based on this algorithmic redundancy. The resulting feature vectors of corresponding points lead unambiguously to an initial orientation of the internal camera network. The latter is done based on a decomposition of the so called essential matrix, which is derived from the initial set of matches. This process is executed taking into account the statistical relevance of each of the hypotheses of the solution, using only a minimal set of points to obtain this solution. The latter asks for respectively 5 or 8 corresponding points between two cameras, depending on whether internal camera parameters (cfr camera calibration) are known. The robust estimation process (eg a RANSAC implementation) provides optimal robustness against outliers.

When available, the camera-to-camera view geometry (the 2-view epipolar geometry) is used to start a constrained image matching process by searching for corresponding points only when they also respect the multiple-view geometry.

Based on this primary orientation the camera heads are adjusted and can be directed towards the shared working volume. This is done by a joined minimisation of the distances between the optical axis of the different cameras and their 3D intersection. The latter is obtained by executing a numerical solver (eg Levenberg-Marquardt) which minimises this cost function. As the optical axes of the different cameras will never intersect in a single point in space but will cross, the center of gravity of the point cloud generated by the midpoints of the shortest (L2 distance) connecting vectors between the different optical axes is used. A valid initialisation is one which, with enough freedom to reorient the camera heads, will converge to a unique solution. Under normal circumstances the outcome, however, will only be an approximation due to a limited number of iterations and finite motion of the heads. After reorienting the camera heads, the cameras self-localisation is re-executed and refined. Given the initial localisation and the knowledge of how the camera heads are re-oriented, the matching process becomes less demanding every iteration, and therefore can be executed faster. This finishes the initial setup of this so called internal camera network. The computation of this initial setup is illustrated in the flowchart of FIG. 7. In FIG. 7 it is also indicated that in case the system can not be bootstrapped the user is asked to take a decision, and eventually will have to adapt the initial multi-view camera network.

In case of a non rigid environment this setup procedure is automatically re-executed whenever necessary. To this end a procedure to self check decides when the latter is necessary. During experiments this was done by checking the back projection error on the computed 3D geometry in the N-view cameras. As a practical threshold an average deviation of 1 pixel can be used. In case no underlying 3D is computed, similarly the deviation with the epipolar geometry can be used as a self check mechanism.

Based on the resulting set of high quality correspondences, the camera configuration or constellation is determined using either auto calibration (if no pre-calibration is available), either the above derived 6 DOF camera mutual localisation is used as an external calibration. A bundle adjustment finalizes the calibration (see FIG. 7 'multi view calibration'). Again, if the calibration is not successful the user is informed about this. At this point the system know the location of the multi view cameras, has possibly adapted the viewing directions of the camera heads, and has performed a full camera calibration.

Secondly a regular endoscope is inserted through the standard entry port. The system of present invention configured so far can be used already as a multi view endoscopic view system. The normal regular endoscopic view is available to the surgeon, whereas on simple request the control unit either switches the view to that of one of the secondary cameras, or shows a tiled overview of one or more cameras on top of the primary image.

The true performance of the system however is only unleashed when the image data is not directly presented to the medical staff, but if it is used as the input for the control unit (cfr. inf.).

Example 2

Multiview Endoscopic Visualisation and Generation of a Synthetic Overview Image or Panorama Implementation of the Optical Large View Endoscopic Systems of Present Invention It is explained beforehand that scene interpretation and analysis—or the 'intelligence' offered by the endoscopic control unit—is what this apparatus really distinguishes from any other endoscopic imaging system.

On the one hand the apparatus can generate a regular endoscopic view, on the other hand the underlying scene model opens the way to a massive set of new technical/medical applications. The presentation of this enhanced information can be done transparently (ie a surgeon is presented subtly enriched information without s/he even realising it) or very explicitly. Examples of both will be provided as an illustration of the application domain. However an exhaustive description of the complete set of possible applications simply is not feasible. We hereunder as embodiments rather provide pointers to general examples and a high level description of the methodology used to implement them:

First Embodiment

Integrating the different video feeds coming from the system described under 'Example 1' leads to a truly enlarged field of view, as a new virtual overview camera can be build. This virtual camera view interpolates smoothly between the real cameras and their real resolutions. This can not only make the new overview possibly an extremely wide angle, but also provides a movable viewpoint without the need for moving cameras. The same is true for adapted resolutions. The exact size of the wide angle is determined by the area of the scene coveted by the multi view cameras.

To this end a set of 'secondary cameras' (minimal two) is inserted, and attached so that the working field can be imaged (see also the description earlier). It is not a prerequisite for these cameras to be fully calibrated beforehand, but having a pre-calibration available increases robustness. Such a pre-calibration is performed using one of the standard techniques described in the literature (eg a "Tsai camera calibration" method). The locations of the cameras and their view directions roughly define the enlarged multi-view volume that will become available.

After insertion, the constellation of the multi-view setup is determined using the techniques of 'Example 1'. If no calibration can be determined, the system falls back to become a mere N-view visualisation unit. The user is informed of this more restricted performance, which in this case is limited to scenes with relatively limited variation in depth. To test this, experiments are performed during which extended retinal overview images are synthesised, without first obtaining a calibration.

Extension of the Embodiment: Continuous Matching and Generating of 3D Information Given the constellation and calibration of the system is known, the orientation of the cameras is adapted to visualise a more overlapping part of the scene as described earlier. This will be done each time the system detects a deviation of the last known constellation (see FIG. 8 'determine corresponding regions/points', 'verify constellation')

Figure 4:
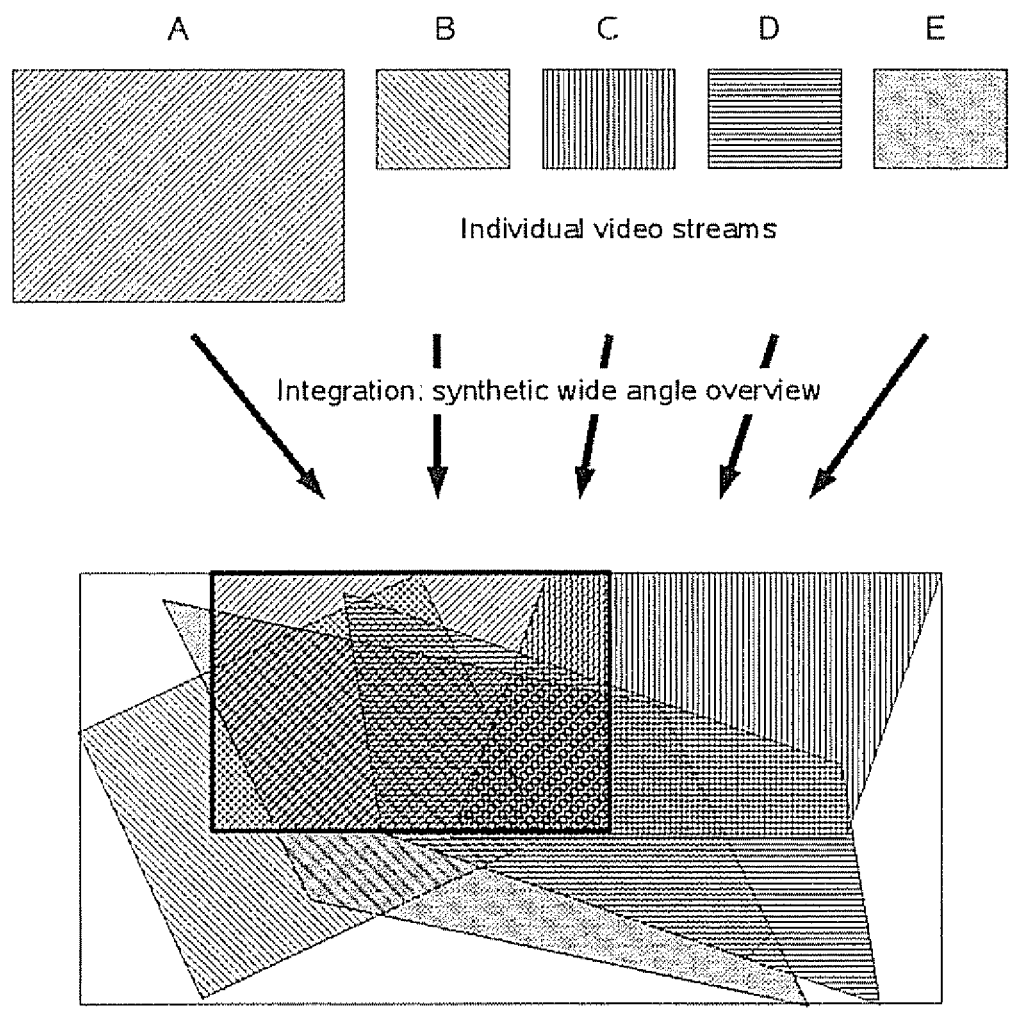
FIG. 4 displays in the top row a schematic representation of the individual camera images from the cameras indicated in FIG. 1-3. The bottom row shows an illustration of a synthesised wide angle image combining all individual camera images or camera video streams. It will be the control unit which provides a solution to this integration problem. As the viewpoints of the different cameras are different, the images will have to be deformed in order to construct this overall integrated synthetic camera image. By sliding a synthetic aperture over this integrated synthetic wide angle camera image, a moving camera with new viewpoints can be generated without moving optics.

From now on the system perpetually will start to generate a set of correspondences based on each image of the cameras. In case of fluent video, the matching process takes also time continuity into account. This operation is executed online, ie the execution of this process is not postponed to a later stage but is done in parallel with the video acquisition. In case of the calibrated setup, 3D localisation of the corresponding feature points now also is performed Extension of the Embodiment: Generating of an Extended Overview Image (see FIG. 4 and FIG. 8)

Given the correspondences between the N views and a sparse set of 3D points, an integrated overview image is generated, and updated at a fixed rate. The latter framerate can be adapted, but can be limited by the amount of computing power available or the use of an excessive number of cameras. The reference implementation can run at 15 hz for 6 cameras. Extended optimisation and further parallelism can improve this framerate.

This generating of an overview image, can be compared to solving a puzzle: each of the multi-view cameras generates a piece of a puzzle. The correspondences determined earlier indicate how to put the pieces together. This however only works if the puzzle has relatively limited depth variation. In all other cases the different pieces can not be outlined consistently anymore. This is overcome by modulating the surface on which we reconstruct this puzzle, based on the 3D information derived earlier. This also explains why, if no calibration could be obtained, the technique will only work for scenes which have relatively limited variation in depth. The implementation uses texture blending with illumination correction on a depth modulated projection surface. These operations can be speeded up using techniques for so called accelerated 3D graphics on a programmable Graphics Programming Unit (GPU).

Extension of the Embodiment: Localisation of the Primary Endoscopic Lens wrt the Synthetic Overview Image (see FIG. 8 'Track Feature Points', 'Rough Localisation Moving Camera', 'Fine Localisation on Overview')

Whereas the earlier described multi view cameras are relatively stable, the primary endoscopic lens inserted can be very mobile. This source of video data can be thought of as a 'spotlight' wandering over the surface being built up. By tracking an extended set of points within the video data generated by this 'primary endoscopic video source' a continuous approximate self localisation can be performed and updated using a standard ego-motion algorithm (sometimes referred to as 'visual odometry'). By relating this to the extended overview images generated, we obtain an accurate localisation within a single coordinate system. The latter is done by pixel based matching, and using a 'position from structure' technique to update the position of the moving camera.

Extension of the Embodiment: Visualisation

The new multi-view image data can be visualised in multiple ways. Either the overview and primary endoscopic image are displayed independently, either an integrated visualisation is shown. In the latter case the localisation relatively wrt the overview can be seamlessly hidden, or in contrary, indicated explicitly on the overview image. The latter can be done using a border indication, or by highlighting of the primary image on the overview. The integrated visualisation is done by showing fine registered textures aligned on the approximate 3D model, or on a (3D modulated) projection surface.

In case of the integrated visualisation, the relative motion and zoom of the visualised video data is no longer restricted to what the real primary endoscopic camera can generate, but extends to the full size of the multi-view endoscopic working volume. This can be considered an example of the subtle (or transparent) visualisation of the enriched information. If it doesn't affect safety considerations (eg in an industrial application) the difference between real and synthetic camera data can be made less apparent.

Example 3

Additional Application Options of the Optical Large View Endoscopic Systems of Present Invention 3.1) If not the synthetic overview images are of primary interest, but the 3D information than the system can generate, the apparatus can be switched to a so called 'dense 3D' modus. Now dense matching at reduced framerates is performed, but depth measurements for as many points as possible are generated. The number of generated points/image strongly depends on the scene under consideration. However, if less than 20% of the image points result in a 3D measurement, the system indicates failure of operation under the current working circumstances. The 3D information in this case results from N (partially) matched views, possibly using a wide baseline constellation. The depth is computed using a standard 2 or 3 view optimal triangulation technique. The technique is called passive 3D reconstruction, as no explicit structured illumination is needed.

3.2) If example 3.1 fails to generate robust data or if higher accuracy is desired, the system can operate in an 'active dense 3D' modus. To this end a source of structured light (or, active illumination) is introduced through the (primary) endoscope. The secondary multi-view cameras now are presented a very apparent set of visual features which facilitate the matching process. It is important to state that the baseline in this system—now between camera and projection system—is again considerably larger than what can be obtained by any other system. By generating adaptable patterns system robustness can be improved, through projection of so called (adaptively) coded structured light. This technique is a so called active technique for 3D reconstruction, again possibly using an extreme wide-baseline setup.

Experiments showed an accuracy using this modus which can be better than 100 micrometer, whereas the average accuracy of the regular 'dense 3D' modus is about 10 times lower 3.3.) The availability of the dense 3D model asks for new visualisation techniques, or at least makes this possible. A particular new application wrt visualisation is the merging of synthetic 3D data and models with the data obtained online through the endoscope. This can be considered an example of an explicit visualisation of the enriched information. In the literature these techniques are mostly referred to as augmented reality or enhanced reality. The availability of the (dense) 3D measurements makes it possible to implement them using endoscopic imaging.

Surgical Applications and Advantages

The endoscopic system of present invention has applications and advantages for critical operations on structures in an enclosed body such as surgery.

1. The enlarged view is demonstrably more important for surgeons with less experience, ie during training, and for those assisting the main surgeon. In animal models it has been shown that it decreases operating time, accidents, bleedings and errors of judgments. Pilot experiments suggest that this will also be true in human surgery.

2. The enlarged view helps with the positioning of instruments in the field of view of the operating camera, thus reducing the problems of stereotaxis and thus decreasing time loss. We anticipate that in randomized trials the conversion rate for eg hysterectomy will be lower. This will constitute a proof that control of bleeding is faster and more accurate.

3. The enlarged view will visualize all the instruments: this will prevent to a large extend the rare accidents caused by this blind manipulation and certainly the accidents, if they occur; will have a much higher probability to be visualized and recognized. We recently reported large and small bowel perforations, with subsequent severe peritonitis, probably caused by a blind instrument since on the video of the surgery itself no injury to the bowel could be seen. If a wide angel view would have been available, the assistant would have had visual control thus preventing accidents, and if nevertheless they would occur, they would have been recognized.

4. The depth enhanced view and localization offers new tools to implement intelligence to increase safety and permit disaster recovery procedures. Firstly regions in which no activity (cutting, clamping, or simply motion . . . ) is to be tolerated can be indicated. The system can give a warning when such an imaginary or real boundary is crossed. Similarly since the synthetic overview image has generated a model of the scene this overview image can be used if the image from the primary camera fails, eg by a vessel pumping blood over the lens. Even if all cameras in the multi-view system would become unavailable (which is unlikely) still the underlying model or synthetic overview image remains available as a good approximation of the real image.

5. The possibly dense depth computation allows for implementing enhanced reality in endoscopy, visualizing and aligning structures generated by other imaging modalities such as CT, MRI etc. The applicability of these enhanced reality techniques is greatly improved by the multi view cameras, as the system becomes also less dependent on external motion tracker systems, and can do better registration. Moreover it offers a means to obtain quantitative 3D information in endoscopy and such to make measurements within a cavity.

An additional difference between the present invention and existing stereo endoscopes or more generally systems used for stereoscopic endoscopy, is that present invention can deduce 3D information from images which for a human observer do not generate a 3D stereo impression when viewed by the observer directly. The latter, however, is the main target of any stereoscopic system.

6. The present system allows to the user or surgeon to per-operatively reorient the lenses and thereby to change the view or field of view of the endoscopic imaging system, which is not possible with a stereo endoscope, as the lenses are rigidly attached to each other at construction time.

7. During surgery orientation of the image remains problematic, since rotation of the camera will rotate the image. Moreover, the restricted field of view (tunnel vision) without clear landmarks indicating horizontal or vertical directions, leads to a situation where a rotated camera view is not perceived as being obviously 'incorrect': there are no visual clues indicating that the perceived situation does not reflect reality in terms of horizontality. Since the camera, and thus also its orientation, generally is controlled by the assistant, this can lead to important errors of judgment. If the camera is, as an example, rotated 45 deg to the left, it results in a situation where the upward direction in the resulting images in fact is pointing to the right side in reality. If the images of the fixed cameras or the points of reference are used to rotate the image of the main camera back to its normal position, a new and effective means of orientation correction is obtained. Also in case of the mono focal setup, a single camera system can be corrected for rotational orientation using the techniques described in present invention. In case the multi camera setup can be used, this correction can be done in a more effective way, which risks to be less error prone.

In other words, present invention allows to do rotational orientation correction of a endoscopic camera view such that the visualized horizontal direction corresponds to the horizontal direction in reality, and this without any external rotation sensor but by image processing only.

The system is very cost effective: the original endoscopic image is available the same way and quality as beforehand as the original imaging pipeline is not modified. Moreover the implementation can run completely transparently.

The invention claimed is:

1. An endoscopic or borescopic vision system for inspecting an inside of a cavity or guiding operation on enclosed structures in said cavity, comprising:
    an imaging system to receive selected images of a target object and to create output signals of the target object image;
    the imaging system comprising a camera system arranged to create output signals of different object images of portions of the target object structure or a direct environment thereof, the camera system comprising a first ocular system and at least a second ocular system, at deployment or in operational working state ocular distances between the first and second ocular systems or relative orientation of the first and second ocular systems arranged to be controllable to change different viewpoints relative to each other;
    the camera system comprising a first and a second camera or multiple secondary cameras designed to create said output signals of different object images of portions of the target object structure or the direct environment thereof based on multiple viewpoint wide baseline imaging, and further comprising an image processing or control arrangement, communicatively coupled to an image acquiring circuitry and configured to process the received signals of the target object image, which cannot be seen by the first camera, and which is under normal working situations not possible with a stereo system,
    the image processing arrangement being arranged to find corresponding image points between the images from different cameras based on a wide baseline matching system and comprising a computer program code arranged to carry out a turnkey technique to find corresponding regions of object images from separate cameras and to direct the cameras of the imaging system towards a shared working volume,
    the ocular systems having re-orientable camera heads configured to automatically fine-tune a field of view of the camera heads,
    wherein a baseline between the first and second ocular systems is arranged to be selectable at deployment or in operational working state in the range 20 to 250 mm, the distance between the ocular systems is arranged to be changeable and wherein the imaging system is configured to determine a configuration or constellation of the camera system fine-tuned using a cognitive control unit and combine the output signals into integrated video data taking into account said configuration or constellation of the camera system, the integrated video data comprising a synthetic overview image, in which generating the synthetic overview image comprises using texture blending with illumination correction on a depth modulated projection surface.

2. The endoscopic or borescopic vision system of claim 1, wherein the distances between the first and second ocular systems are configured to be changeable but wherein at deployment or in an operational working state, the ocular distance is above 50 mm, resulting in a wide baseline vision system, given the size of structures in a scene being imaged during endoscopy.

3. The vision system according to claim 1, the camera system comprising a multi view camera system configured to generate different viewpoints by each of the cameras or to provide several viewpoints of the target object each by different cameras, such that the cameras have a different zoom and orientation.

4. The vision system according to claim 1, wherein the first camera is a principal camera configured to create an object image of the target object on the inside of the cavity to be operated and the second camera or multiple secondary cameras is or are secondary camera or cameras configured to provide an image of another portion of the object.

5. The vision system according to claim 1, wherein the image processing arrangement is configured to transform multiple video streams of the cameras into a synthetic wide angle overview image data in real time and present the image data to the user, and to generate one or more virtual camera images, without the need for motion of any optical components.

6. The vision system according to claim 1, wherein the image processing arrangement is configured to extract 3D information from multiple images of which some are obtainable from a camera that is not mounted to the imaging system.

7. The vision system according to claim 1, wherein the image processing arrangement is configured to generate 3D information based on a projection of structured light through a regular unmodified mono focal endoscope, while imaging the scene through a multi-view endoscopic camera network.

8. The vision system according to claim 1, wherein the image processing arrangement is configured to generate 3D information based on a projection of structured light through a stereo endoscope, while imaging a scene through one optical channel of the endoscope, and projecting through the other optical channel.

9. The vision system according to claim 1, wherein the image processing arrangement is configured to implement a disaster recovery procedure or a safety procedure using an underlying model or synthetic overview image as a good approximation of the target image.

10. The vision system according to claim 1, wherein the image processing arrangement is configured to implement enhanced reality visualization merging endoscopic video data with data coming from another modality based on an interpreted scene data by a cognitive processing arrangement.

11. The vision system of claim 10, wherein said cognitive processing arrangement is configured to use local or distributed intelligence to merge the video data based on scene interpretation.

12. The vision system of claim 1, wherein the secondary camera or multiple secondary cameras are inserted into the cavity using endoscopic or borescopic lenses through secondary entry ports.

13. The vision system of claim 1, wherein the secondary cameras are inserted into the cavity using a flexible endoscopic or flexible borescopic through secondary entry ports.

14. The endoscopic vision system comprising two or more cameras of claim 1 for use in a laparoscopic operation.

\* \* \* \* \*